United States Patent [19]

Holton

[11] 4,246,193

[45] Jan. 20, 1981

[54] PROCESS FOR THE RESOLUTION OF D,1 2-(6-METHOXY-2-NAPHTHYL)PROPIONIC ACID

[75] Inventor: Percy G. Holton, Menlo Park, Calif.

[73] Assignee: Syntex Corporation, Panama

[21] Appl. No.: 97,118

[22] Filed: Nov. 26, 1979

Related U.S. Application Data

[63] Continuation-in-part of Ser. No. 55,258, Jul. 6, 1979, abandoned.

[51] Int. Cl.$^3$ .................... C07C 91/10; A61K 31/205; C07B 19/00; C07C 65/24
[52] U.S. Cl. .............................. 260/501.17; 562/466; 562/401; 424/316; 564/507
[58] Field of Search ...................... 260/501.17, 584 R; 562/466, 401

[56] References Cited

U.S. PATENT DOCUMENTS

| 2,016,962 | 10/1935 | Flint et al. | 260/584 R |
| 2,016,963 | 10/1935 | Flint et al. | 260/584 R |
| 3,904,682 | 9/1975 | Fried et al. | 562/466 |
| 3,904,683 | 9/1975 | Day et al. | 562/466 |
| 3,906,038 | 9/1975 | Fried et al. | 260/501.18 |

OTHER PUBLICATIONS

Greenstein et al., Chem. of the Amimo Acids, John Wiley & Sons, Inc., N.Y., vol. 1, pp. 715-728, (1961).

*Primary Examiner*—Joseph E. Evans
*Assistant Examiner*—G. T. Brettenstein
*Attorney, Agent, or Firm*—Joseph I. Hirsch; John A. Dhuey

[57] ABSTRACT

Mixtures of d 2-(6-methoxy-2-naphthyl)propionic acid and 1 2-(6-methoxy-2-naphthyl)propionic acid or soluble salts thereof are resolved with N-R-D-glucamine or salts thereof, where R is alkyl having 2 to 36 carbon atoms or cycloalkyl having 3 to 8 carbon atoms, to yield a product substantially enriched in d 2-(6-methoxy-2-naphthyl)-propionic acid.

21 Claims, No Drawings

PROCESS FOR THE RESOLUTION OF D,l 2-(6-METHOXY-2-NAPHTHYL)PROPIONIC ACID

CROSS-REFERENCE TO PARENT APPLICATION

This application is a continuation-in-part of application Ser. No. 55,258, filed July 6, 1979, now abandoned.

FIELD OF THE INVENTION

This invention relates to a process for resolving mixtures of d 2-(6-methoxy-2-naphthyl)propionic acid and l 2-(6-methoxy-2-naphthyl)propionic acid to yield a product substantially enriched in d 2-(6-methoxy-2-naphthyl)propionic acid.

d 2-(6-Methoxy-2-naphthyl)propionic acid is a well-known anti-inflammatory, analgesic and anti-pyretic agent which is described and claimed in U.S. Pat. No. 3,904,682. Processes for the preparation of d 2-(6-methoxy-2-naphthyl)propionic acid are described in U.S. Pat. Nos. 3,651,106; 3,652,683; 3,658,858; 3,658,863; 3,663,584; 3,904,682; 3,904,683; and 3,975,432.

BRIEF SUMMARY OF THE INVENTION

In summary, the process of this invention comprises resolving mixtures of d 2-(6-methoxy-2-naphthyl)propionic acid and l 2-(6-methoxy-2-naphthyl)propionic acid or soluble salts thereof with N-R-D-glucamine or a salt thereof, where R is alkyl having 2 to 36 carbon atoms, preferably 2 to 18 carbon atoms, or cycloalkyl having 3 to 8 carbon atoms to yield a product substantially enriched in d 2-(6-methoxy-2-naphthyl)propionic acid, the pharmaceutically active agent. Racemic mixtures of d and l 2-(6-methoxy-2-naphthyl)propionic acid as they occur after known chemical synthesis are the presently preferred starting material for the resolution method of this invention.

The term "alkyl" as used herein refers to and includes straight and branched chain hydrocarbon groups having 2 to 36 carbon atoms. Typical alkyl groups include ethyl, n-propyl, i-propyl, n-butyl, i-butyl, n-hexyl, n-octyl, n-dodecyl, n-octadecyl, n-docosanyl, n-hexatricontanyl, and the like.

The term "cycloalkyl" as used herein refers to and includes cycloaliphatic hydrocarbon groups having 3 to 8 carbon atoms. Typical cycloalkyl groups include cyclopropyl, cyclobutyl, cyclopentyl, cyclohexyl, methylcyclohexyl, cycloheptyl and cyclooctyl. Of the cycloalkyl groups, cyclohexyl is presently preferred.

Presently preferred resolving agents within the scope of this invention are N-n-propyl-D-glucamine, N-n-butyl-D-glucamine, and N-n-octyl-D-glucamine.

The resolution contemplated by this invention is conducted in an inert organic solvent having a pronounced difference between the solubilities of the salt of d 2-(6-methoxy-2-naphthyl)propionic acid with the resolving agent and the salt of l 2-(6-methoxy-2-naphthyl)propionic acid with the resolving agent, generally at temperatures between room or ambient temperature and an elevated temperature generaly up to the reflux temperature of the solvent utilized. The salt of d 2-(6-methoxy-2naphthyl)propionic acid with the resolving agent (for example, N-n-propyl-D-glucamine, N-n-butyl-D-glucamine or N-n-octyl-D-glucamine) should be significantly less soluble in the solvent than is the salt of l 2-(6-methoxy-2-naphthyl)propionic acid with the resolving agent and, accordingly, upon the cooling of a heated solution thereof, generally to or about ambient or room temperature, such salt of d 2-(6-methoxy-2-naphthyl)propionic acid with the resolving agent will be preferentially crystallized therefrom. Suitable solvents include water, $C_1$ to $C_{10}$ monohydric alcohols, such as, for example, methanol, ethanol, n-propanol, isopropanol, butanol, pentanol, hexanol, cyclohexanol, 2-ethylhexanol, benzyl alcohol, furfuryl alcohol, and the like, $C_2$ to $C_6$ dihydric alcohols, such as, for example, ethylene glycol, 1,2-propylene glycol, 1,3-propylene glycol, and the like, $C_3$ to $C_4$ trihydric alcohols, such as for example, glycerol, and the like, $C_3$ to $C_{11}$ ketones, such as, for example, acetone, acetylacetone, ethyl methyl ketone, diethyl ketone, di-n-propyl ketone, diisopropyl ketone, diisobutyl ketone, and the like. Other solvents include mono- and di(lower)alkyl ether of ethylene glycol and diethylene glycol, dimethylsulfoxide, sulfolanes, formamide, dimethylformamide, N-methyl pyrrolidone, pyridine, dioxane, dimethylacetamide, and the like. The $C_1$ to $C_3$ alcohols, e.g. methanol and isopropanol, particularly methanol, are the presently preferred solvents. Sufficient water can be added to the solvent if needed to solubilize all of the materials which have been added thereto.

The starting material [i.e., the mixture of d 2-(6-methoxy-2-naphthyl)propionic acid and l 2-(6-methoxy-2-naphthyl)propionic acid or soluble salts thereof] is heated to an elevated temperature, generally to a temperature in the range from about 60° C. to about 100° C. or the reflux temperature of the solvent, in the presence of the resolving agent to solubilize all of the materials which have been added to the solvent. If desired, the solvent can be held at the elevated temperature until all of the materials have gone into solution. After the solution has been held at the elevated temperature for the desired length of time, it is slowly cooled to ambient temperature. During the cooling process, the solution is preferably seeded with a salt of d 2-(6-methoxy-2-naphthyl)propionic acid and the resolving agent [e.g., the salt of d 2-(6-methoxy-2-naphthyl)propionic acid with N-n-propyl-D-glucamine]. The crystalline precipitate which results is enriched in the salt of d 2-(6-methoxy-2-naphthyl)propionic acid with the resolving agent. The final temperature to which the solution is taken is chosen by practical considerations but generally is selected so that the temperature difference will be sufficient to provide a high yield of crystals. The crystallizing mixture can be maintained at the lower temperature until crystallization is complete, or nearly so, usually for about 30 minutes to about several hours or so. The crystalline precipitate which results is removed by filtration and washed.

The crystalline material which is obtained at this stage in the process [i.e., a material which is enriched in the salt of d 2-(6-methoxy-2-naphthyl)propionic acid with the resolving agent], after separation by filtration and washing, can be charged to water and heated, if necessary, to redissolve the crystalline material. For those N-R-D-glucamines which are soluble in water, the resulting solution is acidified for example with a mineral acid, such as sulphuric acid or hydrochloric acid, or an organic acid such as acetic acid, and the crystalline precipitate so obtained is separated by filtration, washed and dried. There results a white crystalline product substantially enriched in d 2-(6-methoxy-2-naphthyl)propionic acid. Alternatively, for those N-R-D-glucamines which are insoluble in water, the material enriched in the salt of d 2-(6-methoxy-2-naphthyl)propionic acid with such a resolving agent can be treated with a strong base, such as, for example, potassium hydroxide or other strong base having a pKa vaue greater than 10, to cleave the salt, followed by filtration to remove the resolving agent and acidification of the filtrate with, for example, a mineral acid such as hydrochloric acid or sulfuric acid, or an organic acid such as acetic acid, to give, after filtration, washing and drying, a white crystalline product substantially enriched in d 2-(6-methoxy-2-naphthyl)propionic acid.

Prior to the cleavage of the material enriched in the salt of d 2-(6-methoxy-2-naphthyl)propionic acid with the resolving agent to obtain d 2-(6-methoxy-2-naphthyl)propionic acid, it is generally desirable to redissolve the enriched salt material in further solvent material, heat the solvent to the desired (normally elevated) temperature, seed the resultant solution with the salt of d 2-(6-methoxy-2-naphthyl)propionic acid with the resolving agent, and cool the resultant solution to effect one or more further recrystallizations. Each such recrystallization further increases the proportion of the salt of d 2-(6-methoxy-2-naphthyl)propionic acid with the resolving agent in the recrystallized material. N-n-propyl-D-glucamine, N-n-butyl-D-glucamine, and N-n-hexyl-D-glucamine are particularly suitable resolving agents within the scope of this invention because, with merely one recrystallization step prior to the redissolution of the resultant crystalline product and subsequent acidification, a product having a purity on the order of about 97–99% d 2-(6-methoxy-2-naphthyl)propionic acid can be obtained.

N-n-ocytl-D-glucamine, however, is the presently preferred resolving agent because, with use of N-n-octyl-D-glucamine, the salt of d 2(6-methoxy-2-naphthyl)propionic acid with N-n-octyl-D-glucamine is readily recoverable by filtration, d 2-(6-methoxy-2-naphthyl)propionic acid of acceptably high optical purity can be obtained without need for one or more recrystallizations prior to the cleaving step, and the resolving agent can be recovered directly and in high yield (on the order of about 97–98%) by filtration. Additionally, the cleavage can be conducted under either alkaline or acidic conditions. Alkaline cleavage results in a precipitate of N-n-octyl-D-glucamine while the d 2-(6-methoxy-2-naphthyl)propionic acid remains in solution in the alkaline medium. Acidic cleavage results in a precipitate of d 2-(6-methoxy-2-naphthyl)propionc acid while the N-n-octyl-D-glucamine remains in solution in the acidic medium.

The N-n-octyl-D-glucamine is substantially insoluble in water, thus permitting recovery thereof in high yields from aqueous systems. This is also true for other resolving agents of this invention where R is alkyl having at least 6 carbon atoms, e.g., those resolving agents where R is alkyl having from 6 to 18 carbon atoms.

The material enriched in l 2-(6-methoxy-2-naphthyl)propionic acid or the N-R-D-glucamine salt thereof (where R is as defined above) can be processed to recover l 2-(6-methoxy-2-naphthyl)propionic acid which can then be racemized according to known techniques to give a material having a higher content of d 2-(6-methoxy-2-naphthyl)propionic acid. See, for example, Dyson U.S. Pat. No. 3,686,183. This material can be recycled, either alone or in combination with other d,l 2-(6-methoxy-2-naphthyl)propionic acid, to provide additional starting material for the resolution process of this invention.

The amount of resolving agent employed [on a molar basis relative to the d,l 2-(6-methoxy-2-naphthyl)propionic acid being resolved] in accordance with the present invention ranges from between about 50% and 100%. However, as only about 50% [on a molar basis relative to the d,l 2-(6-methoxy-2-naphthyl)propionic acid being resolved] of the resolving agent is needed to form the more insoluble salt thereof with the d 2-(6-methoxy-2-naphthyl)propionic acid, the remainder of the resolving agent (generally on the order of up to about 40–50 molar %) can be replaced, if desired, with a more inexpensive base, including, for example, an inorganic base such as an alkali metal hydroxide, such as sodium hydroxide or potassium hydroxide, or an organic tertiary amine such as triethylamine, triethanolamine, tributylamine, etc.

The aqueous mother liquors resulting from the isolation of d 2-(6-methoxy-2-naphthyl)propionic acid and l 2-(6-methoxy-2-naphthyl)propionic acid contain, for example, salts of the resolving agent with the acid utilized in the acidification step. Such mother liquors can be treated with an inorganic base to form the corresponding insoluble salt with the N-R-D-glucamine, such as, for example, treatment with a suspension of calcium hydroxide to precipitate the corresponding calcium salt, which is removed by filtration. The filtrate is concentrated under vacuum at elevated temperatures to dryness, first removing any further salt, e.g. the calcium salt, which is formed during the early stages of the concentration process. The residue is dissolved in a suitable solvent at an elevated temperature up to the reflux temperature of the solvent, and then cooled to room temperature, to thereby afford the resolving agent as a crystalline precipitate which can be reused, either alone or in combination with new material, in the resolution process of this invention. Alternatively, the resolving agent can be recovered through use of an anion exchange resin and recycled for reuse.

The terms "mixture of d 2-(6-methoxy-2-naphthyl)propionic acid and d 2-(6-methoxy-3-naphthyl)propionic acid" is also intended to include those salts thereof which are soluble in the solvent utilized in the resolution process of this invention. Such salts include, for example, the corresponding sodium salts, potassium salts, lithium salts, and the like. Such salts can be prepared by the addition of base, such as an alkali metal hydroxide, for example, sodium or potassium hydroxide, to a solution of the mixture of the d and l 2-(6-methoxy-2-naphthyl)propionic acid. The resulting mixture of d 2-(6-methoxy-2-naphthyl)propionic acid and l 2-(6-methoxy-2-naphthyl)propionic acid salts can be resolved according to the present invention by use of a salt of the resolving agent which will react to form a salt of d 2-(6-methoxy-2-naphthyl)propionic acid with the N-R-D-glucamine. Suitable glucamine salts include, for example, the hydrochloride salt and the acetate salt. Other salts include the propionate salt, butyrate salt, isobutyrate salt, sulfate salt, nitrate salt, and the like. Accordingly, the term "N-R-D-glucamine" (Where R is as defined above) is intended to include those salts thereof which, when used with an appropriate salt of the mixture of d and l 2-(6-methoxy-2-naphthyl)propionic acid, will afford the resolution contemplated hereby.

The N-R-D-glucamine salts of d 2(6-methoxy-2-naphthyl)propionic acid are useful as anti-inflammatory, analgesic, and/or antipyretic agents, platelet aggregation inhibitors, fibrinolytic agents and as smooth muscle relaxants. The aforesaid salts are also useful in the treatment of dysmenorrhoea and are agents for alleviating post-menopausal symptoms.

Accordingly, such salts would be useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, such salts would be useful for the relief of these conditions as well as the inflammation.

Administration of the aforesaid salts in an appropriate pharmaceutical composition can be via any of the accepted modes of administration of agents for the treatment of inflammation, pain, or pyrexia. Thus, administration can be, for example, orally, parenterally (as by, e.g., injection), or topically, in the form of solid, semi-solid or liquid dosage forms, such as, for example, tablets, suppositories, pills, capsules, powders, liquid solutions, suspensions, creams, lotions, ointments, or the like, preferably in unit dosage forms suitable for simple administration of precise dosages. Such pharmaceutical compositions will include a conventional pharmaceutical carrier or excipient and a salt of N-R-D-glucamine with d 2-(6-methoxy-2-naphthyl)propionic acid, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 2 mg. to 20 mg. of the aforesaid salt per kilogram of body weight is used. For such oral administration, a pharmaceutically acceptable non-toxic composition is formed by an incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

A suppository using, for example, polyalkylene glycols, such as polypropylene glycol, as the carrier can be formulated. Liquid pharmaceutically administerable compositions can, for example, be prepared by dissolving, dispersing, etc. the aforesaid salt and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifing agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences,* Mack Publishing Company, Easton, Pennsylvania, 14th Edition, 1970. The composition to be administered will, in any event, contain a quantity of the aforesaid salt(s) in a pharmaceutically effective amount for relief of the particular condition being treated in accordance with the teachings hereof.

The aforesaid salts are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the aforesaid salts may not maintain the pregnant state for an indefinite period of time. Rather, in such instances, the pregnancy will, most probably, be slightly "prolonged", a factor which may be advantageous to either the mother and/or the fetus.

The aforesaid salts are also used as agents for delaying the onset of, or for postponing, parturition. As used in this application, the phrase "to delay the onset of parturition" is intended to cover that delay in parturition caused by the administration of one of the aforesaid salts at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy which the fetus is considered to be "viable". In either case, the agents are administered as prophylatic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time considered favorable to the mother and/or fetus.

As used in this application, the phrase "postponing parturition" is intended to cover that delay in parturition caused by the administration of one of the aforesaid salts after uterine muscle contraction have begun. The condition of the patient, including the time within the gestation period when the contractions have begun, the severity of the contractions and how long the contractions have taken place will affect the results achieved. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

With respect to animals, this treatment can also be utilized to synchronize the deliveries from a group of pregnant animals to happen at or about the same time, or to happen at or about a desired time and/or place, when the births can be handled with greater facility.

In all cases, administration should be consistent with best and/or accepted medical (or veterinary) practices so as to maximize the benefits to the mother and the fetus. For example, administration should not be continued so long past full term that the fetus dies in utero.

In the practice of this aspect of the present invention, a therapeutically effective amount of one of the aforesaid salts or a pharmaceutical composition containing an aforesaid salt is administered to the pregnant mammal via any of the usual and acceptable methods known in the art. The salt can be administered either singly or in combination with another compound or compounds, as defined above, or other pharmaceutical agents, carriers, adjuvants, etc. Such salt(s) or compositions can be administered orally or parenterally in the doses and in the forms (including oral, vaginal or uterine tablets or suppositories, etc.) as set forth above regarding anti-inflammatory, etc. activities. Administration can be a single daily dose or up to 3 or 4 smaller doses regularly given throughout the day. The actual amount of the salt administered will, of course, depend on its relative activity for this particular utility.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

18 G. of D-glucose, 20 ml. of 70% ethylamine in water and 1 g. of Raney Nickel in 140 ml. of methanol and 30 ml. of water are treated with hydrogen at 160 psi for 2 hours at 60° C. The solution is filtered to remove the catalyst, the solvent concentrated at low pressure, the precipitate dissolved in 50 ml. of methanol, and the resultant solution filtered and cooled to give 15.5 g. of N-ethyl-D-glucamine [m.p. 132°–134° C.; $[\alpha]_D$-15.4° (water)] as a precipitate.

PREPARATION 2

18 G. of D-glucose, 20 ml. of n-propylamine and 1 g. of Raney Nickel in 140 ml. of methanol and 40 ml. of water are treated with hydrogen at 160 psi for 2 hours at 60° C. 40 Ml. of water is added to dissolve the precipitate, the solution is filtered to remove the catalyst, the solvent concentrated at low pressure, the residue dissolved in 100 ml. of methanol, and the resultant solution cooled to give 14.6 g. of N-n-propyl-D-glucamine [m.p. 141°–143° C.; $[\alpha]_D$-15.2° (water)] as a precipitate.

PREPARATION 3

9 G. of D-glucose is mixed with 9 g. of iso-propylamine for 2 hours, 5 ml. of ethanol is added and the mixture stirred overnight. The excess isopropylamine and the ethanol are removed at low pressure, the residue is dissolved in 180 ml. of methanol and treated overnight at 50° C. with 1 g. of 5% Palladium on charcoal and hydrogen (176 psi). The methanol solution is filtered to remove the catalyst, concentrated at low pressure, and the resultant residue recrystallized from ethanol to give 5.7 g. of N-isopropyl-D-glucamine [m.p. 134°–136° C.; $[\alpha]_D$-13.5° (water)].

PREPARATION 4

18 G. of D-glucose is mixed with 21.9 g. of n-butylamine and 180 ml. of methanol at reflux for one hour, the excess n-butylamine and the methanol are removed at low pressure, and the residue is dissolved in 180 ml. of methanol and treated overnight at 60° C. with 1.5 g. of 5% Palladium on charcoal and hydrogen (180 psi). The solution is filtered to remove the catalyst, concentrated at low pressure, and the resultant residue recrystallized from ethanol to give 13.3 g. of N-n-butyl-D-glucamine [m.p. 129°–131° C.; $[\alpha]_D$-14.30° (water)].

PREPARATION 5

18 G. of D-glucose, 22 g. of iso-butylamine and 1 g. of Raney Nickel in 140 ml. of methanol and 40 ml. of water are treated with hydrogen at 160 psi for 2 hours at 60° C. The solution is filtered to remove the catalyst, and stored overnight at −10° C. to give a precipitate which is recovered by filtration. 6.6 G. of N-iso-butyl-D-glucamine [m.p. 138°–143° C.; $[\alpha]_D$-18.8° (dimethylsulfoxide) is obtained.

PREPARATION 6

18 G. of D-glucose, 9.9 g. of cyclohexylamine and 1 g. of Raney Nickel in 140 ml. of methanol and 40 ml. of water are treated with hydrogen at 160 psi for 2 hours at 60° C. The solution is filtered to remove the catalyst, and stored overnight at −10° C. to give a precipitate which is recovered by filtration. 2.35 G. of N-cyclohexyl-D-glucamine [m.p. 144°–146° C.; $[\alpha]_D$−20.4° (dimethylsulfoxide)] is obtained.

PREPARATION 7

18 G. of D-glucose, 25 ml. of n-octylamine and 1 g. of Raney Nickel in 140 ml of methanol and 40 ml of water are treated with hydrogen at 160 psi for 3 hours at 60° C. The reaction mixture is slurried with 300 ml. of dichloromethane to dissolve most of the resultant precipitate, filtered to remove the catalyst, and concentrated at low pressure to give 9.2 g. of N-n-octyl-D-glucamine [m.p. 120°–122° C.; $[\alpha]_D$−16.6° (dimethylsulfoxide)].

PREPARATION 8

18 G. of D-glucose, 18.5 g. of n-dodecylamine and 1 g. of Raney nickel in 140 ml. of methanol and 40 ml. of water are treated with hydrogen at 160 psi for 2 hours at 60° C. The solution is filtered to remove the catalyst, and stored overnight at −10° C. The precipitate (20.35 g.) which results is recovered by filtration. 10 G. of the latter and 1 g. of Raney Nickel in 200 ml. of methanol are treated overnight with hydrogen at 180 psi at 60° C. The reaction with hydrogen is then continued for an additional 3.5 hours at 180 psi and 105° C. The reaction mixture is heated to dissolve a precipitate which results, and filtered to remove the catalyst. The reaction mixture is cooled to room temperature, held at that temperature for 2 hours, then filtered to give 4.59 g. of N-n-dodecyl-D-glucamine [m.p. 122°–125° C.; $[\alpha]_D$−14.0° (dimethylsulfoxide)].

PREPARATION 9

18.0 G. of glucose and 27.0 g. of n-octadecylamine are stirred in 500 ml. of methanol for approximately 60 hours. The precipitate which forms is collected, washed with about 250 ml. of methanol and then dried under vacuum (with a slight nitrogen bleed) at about 53° C. to thereby afford 39.5 g. of collected material. 2.0 G. of the latter is mixed with 0.5 g. of 5% palladium on charcoal in 200 ml. of isopropanol and treated with hydrogen (300 psi) overnight at 50° C. The precipitate which results is dissolved by heating the solvent. The reaction mixture is filtered through celite to remove the catalyst and cooled to give 1.5 g. of N-n-octadecyl-D-glucamine (m.p. 124°–126° C.). 0.4 G. of the latter is dissolved in 20 ml. of heated isopropanol, filtered and cooled to give 0.36 g. of purified N-n-octadecyl-D-glucamine [m.p. 123°–126° C., $[\alpha]_D$−10.6° (pyridine)].

PREPARATION 10

18.0 G. of glucose and 10.1 g. of n-hexylamine are stirred at room temperature in 145 ml. of methanol for approximately 60 hours. The reaction mixture is mixed with 1.0 g. of 5% palladium on charcoal and treated with hydrogen (100 psi) overnight at 45°–50° C. The precipitate which forms is collected and redissolved in 200 ml. of methanol, filtered through celite to remove the catalyst, and cooled to give 15.03 g. of N-n-hexyl-D-glucamine [m.p. 125°–126° C.; $[\alpha]_D - 18.6°$ (dimethylsulfoxide)] as a precipitate.

EXAMPLE 1

4.60 G. of d,l 2-(6-methoxy-2-naphthyl)propionic acid is heated with 1.01 g. of triethylamine (0.5 equivalent) in 35 ml. of isopropanol to about the reflux temperature of the solvent to dissolve the d,l 2-(6-methoxy-2-naphthyl)propionic acid. 2.09 G of N-ethyl-D-glucamine (0.5 equivalent) are added and the solution is cooled to room temperature (i.e. about 20°–23° C.) to give 4.42 g. of a material enriched in the salt of d 2-(6-methoxy-2-naphthyl)propionic acid with N-ethyl-D-glucamine (m.p. 153°–161° C.). A sample of the latter is dissolved in about 25 ml. of water heated to about 80° C., treated with hydrochloric acid until acidic at which time a material enriched in d 2-(6-methoxy-2-naphthyl)-propionic acid precipitates out of solution and is recovered by filtration ($[\alpha]_D + 27.7°$ (chloroform)).

1.00 G. of the material enriched in the salt of d 2-(6-methoxy-2-propionic acid with N-ethyl-D-glucamine is dissolved in 19.5 ml. of isopropanol and 1.5 ml. of water at about the reflux temperature of the solvent. The solution is cooled to room temperature to give 0.65 g. of a recrystallized salt (m.p. 167°–169° C.). This material is treated with hydrochloric acid as set forth above in the preceding paragraph to give a material further enriched in d 2-(6-methoxy-2-naphthyl)propionic acid ($[\alpha]_D + 56.0°$ (chloroform)).

EXAMPLE 2

4.60 G. of d,l 2-(6-methoxy-2-naphthyl)propionic acid is heated with 1.01 g. of triethylamine (0.5 equivalent) in 30 ml. of isopropanol and 1.5 ml of water to about the reflux temperature of the solvent to dissolve the d,l 2-(6-methoxy-2-naphthyl)propionic acid. 2.09 G. of N-ethyl-D-glucamine are added and the solution is cooled to room temperature to give 4.32 g. of a material enriched in the salt of d 2-(6-methoxy-2-naphthyl)propionic acid with N-ethyl-D-glucamine (m.p. 149°–156° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 35.9°$).

1.00 G. of the material enriched in the salt of d 2-(6-methoxy-2-naphthyl)propionic acid with N-ethyl-D-glucamine is dissolved in 20 ml. of 5% aqueous isopropanol and 1.0 ml of water at about the reflux temperature of the solvent. The solution is cooled to room temperature to give 0.70 g. of a first recrystallized material (m.p. 167°–168° C.). A sample of the latter is treated with hydrochloric acid as set forth in the preceding paragraph to give a material further enriched in d 2-(6-methoxy-2-naphthyl)propionic acid ($[\alpha]_D + 55.4°$).

0.50 G. of the first recrystallized material from the preceding paragraph [i.e. the material enriched in the salt of d 2-(6-methoxy-2-naphthyl)propionic acid with N-ethyl-D-glucamine] is dissolved in 10 ml. of 5% aqueous isopropanol and 0.5 ml. of water at about the reflux temperature of the solvent. The solution is cooled to room temperature to give 0.43 g. of a second recrystallized material (m.p. 169°–170° C.). A sample of the latter is treated with hydrochloric acid as set forth in the first paragraph of this Example to give a material even further enriched in d 2-(6-methoxy-2-naphthyl)propionic acid ($[\alpha]_D + 62.0°$).

0.33 G. of the second recrystallized material from the preceding paragraph [i.e., the material further enriched in the salt of d 2-(6-methoxy-2-naphthyl)-propionic acid with N-ethyl-D-glucamine] is dissolved in 12 ml. of 5% aqueous isopropanol and 1.0 ml. of water at about the reflux temperature of the solvent. The solution is cooled to room temperature to give 0.27 g. of a third recrystallized material. The latter is treated with hydrochloric acid as set forth in the first paragraph of this Example to give substantially pure d 2-(6-methoxy-2-naphthyl)propionic acid ($[\alpha]_D + 67.1°$).

EXAMPLE 3

2.30 G. of d,l 2-(6-methoxy-2-naphthyl)propionic acid is heated with 0.5 g. of triethylamine in 23 ml. of denatured ethanol to about the reflux temperature of the solvent to dissolve the d,l 2-(6-methoxy-2-naphthyl)propionic acid. 1.05 G. of N-ethyl-D-glucamine are added, and the solution is seeded with a small amount of the salt of d 2-(6-methoxy-2-naphthyl)propionic acid with N-ethyl-D-glucamine and then cooled to room temperature to give 1.95 g. of a material enriched in the salt of d 2-(6-methoxy-2-naphthyl)propionic acid with N-ethyl-D-glucamine (m.p. 157°–160° C.). A sample of the latter is dissolved in about 25 ml. of water heated to about 80° C., treated with hydrochloric acid until acidic at which time a material enriched in d 2-(6-methoxy-2-naphthyl)-propionic acid precipitates out of solution and is recovered by filtration ($[\alpha]_D + 38.1°$).

1.0 G. of the material enriched in the salt of d 2-(6-methoxy-2-naphthyl)propionic acid with N-ethyl-D-glucamine is dissolved in 15 ml. of the denatured ethanol at about the reflux temperature of the solvent. The solution is slowly cooled, seeded with a small amount of the salt of d 2-(6-methoxy-2-naphthyl)propionic acid with N-ethyl-D-glucamine, and then further cooled to room temperature to give, after recovery by filtration, 0.65 g. of a material enriched in the salt of d 2-(6-methoxy-2-naphthyl)propionic acid with N-ethyl-D-glucamine (m.p. 167°–168° C.). A sample of the latter is dissolved in about 25 ml. of water heated to about 80° C., treated with hydrochloric acid until acidic at which time a material enriched in d 2-(6-methoxy-2-naphthyl)-propionic acid precipitates out of solution and is recovered by filtration ($[\alpha]_D + 61.6°$).

EXAMPLE 4

4.60 G. of d,l 2-(6-methoxy-2-naphthyl)propionic acid is heated with 1.01 g. of triethylamine (0.5 equivalent) in 35 ml. of isopropanol to about the reflux temperature of the solvent to dissolve the d,l 2-(6-methoxy-2-naphthyl)-propionic acid. 2.23 G. of N-n-propyl-D-glucamine (0.5 equivalent) are added and the solution is cooled to room temperature to give 4.68 g. of a material enriched in the salt of d 2-(6-methoxy-2-naphthyl)propionic acid with N-n-propyl-D-glucamine (m.p. 173°–175° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 46.4°$).

1.00 G. of the material enriched in the salt of d 2-(6-methoxy-2-naphthyl)propionic acid with N-n-propyl-D-glucamine is dissolved in 19.5 ml. of isopropanol and 2.5 ml. of water at about the reflux temperature of the solvent. The solution is cooled to room temperature to give 0.82 g. of a recrystallized salt (m.p. 180°–181° C.). This material is treated with hydrochloric acid as set forth in the preceding paragraph to give substantially pure 2-(6-methoxy-2-naphthyl)propionic acid ($[\alpha]_D + 68.0°$).

EXAMPLE 5

4.60 G. of d,l 2-(6-methoxy-2-naphthyl)propionic acid is heated with 1.01 g. of triethylamine (0.5 equivalent) in 35 ml. of isopropanol to about the reflux temperature of the solvent to dissolve the d,l 2-(6-methoxy-2-naphthyl)propionic acid. 2.23 G. of N-iso-propyl-D-glucamine (0.5 equivalent) are added and the solution is cooled to room temperature give 4.43 g. of a material enriched in the salt of d 2-(6-methoxy-2-naphthyl)propionic acid with N-iso-propyl-D-glucamine. A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 28.8°$).

1.00 G. of the material enriched in the salt of d 2-(6-methoxy-2-naphthyl)propionic acid with N-isopropyl-D-glucamine is dissolved in 21 ml. of 5% aqueous isopropanol at about the reflux temperature of the solvent. The solution is cooled to room temperature to give 0.85 g. of a recrystallized salt. The latter is treated with hydrochloric acid as set forth in the preceding paragraph to give a material further enriched in d 2-(6-methoxy-2-naphthyl)propionic acid ($[\alpha]_D + 42.7°$).

EXAMPLE 6

4.60 G. of d,l 2-(6-methoxy-2-naphthyl)propionic acid is heated with 1.01 g. of triethylamine (0.5 equivalent) in 30 ml. of isopropanol and 1.5 ml of water to about the reflux temperature of the solvent to dissolve the d,l 2-(6-methoxy-2-naphthyl)propionic acid. 2.23 G. of N-iso-propyl-D-glucamine are added and the solution is cooled to room temperature to give 4.38 g. of a material enriched in the salt of d 2-(6-methoxy-2-naphthyl)propionic acid with N-iso-propyl-D-glucamine (m.p. 146°–148° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 26.9°$).

1.00 G. of the material enriched in the salt of d 2-(6-methoxy-2-naphthyl)propionic acid with N-isopropyl-D-glucamine is dissolved in 20 ml. of 5% aqueous isopropanol at about the reflux temperature of the solvent. The solution is cooled to room temperature to give 0.76 g. of a first recrystallized material (m.p. 151°–152° C.). A sample of the latter is treated with hydrochloric acid as set forth in the preceding paragraph to give a material further enriched in d 2-(6-methoxy-2-naphthyl)propionic acid ($[\alpha]_D + 43.0°$).

0.50 G. of the first recrystallized material from the preceding paragraph [i.e. the material enriched in the salt of d 2-(6-methoxy-2-naphthyl)propionic acid with N-isopropyl-D-glucamine] is dissolved in 10 ml. of 5% aqueous isopropanol at about the reflux temperature of the solvent. The solution is cooled to room temperature to give 0.43 g. of a second recrystallized material (m.p. 153°–154° C.). A sample of the latter is treated with hydrochloric acid as set forth in the first paragraph of this Example to give a material even further enriched in d 2-(6-methoxy-2-naphthyl)propionic acid ($[\alpha]_D + 53.2°$).

0.32 G. of the second recrystallized material from the preceding paragraph [i.e. the material further enriched in the salt of d 2-(6-methoxy-2-naphthyl)-propionic acid with N-isopropyl-D-glucamine] is dissolved in 10 ml. of 5% aqueous isopropanol at about the reflux temperature of the solvent. The solution is cooled to room temperature to give 0.29 g. of a third recrystallized material (m.p. 153°–154° C.). The latter is treated with hydrochloric acid as set forth in the first paragraph of this Example to give a material yet further enriched in d 2-(6-methoxy-2-naphthyl)propionic acid ($[\alpha]_D + 57.9°$).

EXAMPLE 7

4.60 G. of d,l 2-(6-methoxy-2-naphthyl)propionic acid is heated with 1.01 g. of triethylamine (0.5 equivalent) in 18 ml. of ethanol to about the reflux temperature of the solvent to dissolve the d,l 2-(6-methoxy-2-naphthyl)propionic acid. 2.37 G. of N-n-butyl-D-glucamine and an additional 18 ml. of ethanol are added and the solution is cooled to room temperature to give 4.28 g. of a material enriched in the salt of d 2-(6-methoxy-2-naphthyl)propionic acid with N-n-butyl-D-glucamine (m.p. 155°–156° C.). 1.0 G. of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 27.4°$).

3.0 G. of the material enriched in the salt of d 2-(6-methoxy-2-naphthyl)propionic acid with N-n-butyl-D-glucamine is dissolved in 48 ml. of ethanol and 1 ml. of water at about the reflux temperature of the solvent. The solution is cooled to room temperature to give 2.64 g. of a recrystallized salt (m.p. 157.5°–158° C.). 1.0 G. of the latter is treated with hydrochloric acid as set forth in the preceding paragraph to give substantially pure d 2-(6-methoxy-2-naphthyl)propionic acid ($[\alpha]_D + 65.8°$).

EXAMPLE 8

0.28 G. of potassium hydroxide is dissolved in 18 ml of methanol, then 2.30 g. of d,l 2-(6-methoxy-2-naphthyl)-propionic acid and 1.18 g. of N-n-butyl-D-glucamine are added and the methanolic solution heated to about the reflux temperature of the solvent to dissolve the d,l 2-(6-methoxy-2-naphthyl)propionic acid. The solution is slowly cooled, seeded with a small amount of the salt of d 2-(6-methoxy-2-naphthyl)propionic acid with N-n-butyl-D-glucamine, and then further cooled to room temperature to give, after recovery by filtration and washing, 1.18 g of a material enriched in the salt of d 2-(6-methoxy-2-naphthyl)propionic acid with N-n-butyl-D-glucamine. The latter is dissolved in 15 ml of water heated to about 80° C., treated with hydrochloric acid until acidic at which time 0.56 g of a material enriched in d 2-(6-methoxy-2-naphthyl)propionic acid precipitates out of solution and is recovered by filtration ($[\alpha]_D + 56.8°$).

EXAMPLE 9

2.30 G. of d,l 2-(6-methoxy-2-naphthyl)propionic acid and 0.50 g. of triethylamine (0.5 equivalent) are dissolved in 25 ml. of acetone. 1.19 G. of N-n-butyl-D-glucamine is heated in an additional 25 ml. of acetone to 50° C. 3.5 Ml. of water in 0.5 ml. increments is added to solubilize the N-n-butyl-D-glucamine. The N-n-butyl-D-glucamine solution is added to the solution of d,l 2-(6-methoxy-2-naphthyl)propionic acid at 50° C. with stirring, then cooled to room temperature to give 1.83 g. of a material enriched in the salt of d 2-(6-methoxy-2-naphthyl)propionic acid with N-n-butyl-D-glucamine (m.p. 157°-158° C. A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 61.1°$).

EXAMPLE 10

4.60 G. of d,l 2-(6-methoxy-2-naphthyl)propionic acid is heated with 1.01 g. of triethylamine (0.5 equivalent) in 40 ml. of isopropanol and 2.0 ml of water to about the reflux temperature of the solvent to dissolve the d,l 2-(6-methoxy-2-naphthyl)propionic acid. 2.37 G. of N-iso-butyl-D-glucamine are added and the solution is cooled to room temperature to give 4.53 g. of a material enriched in the salt of d 2-(6-methoxy-2-naphthyl)propionic acid with N-iso-butyl-D-glucamine (m.p. 150°-152° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 30.2°$).

1.00 G. of the material enriched in the salt of d 2-(6-methoxy-2-naphthyl)propionic acid with N-iso-butyl-D-glucamine is dissolved in 20 ml. of 5% aqueous isopropanol at about the reflux temperature of the solvent. The solution is cooled to room temperature to give 0.85 g. of a first recrystallized material (m.p. 154°-156° C.). A sample of the latter is treated with hydrochloric acid as set forth in the preceding paragraph to give a material further enriched in d 2-(6-methoxy-2-naphthyl)propionic acid ($[\alpha]_D + 40.3°$).

0.80 G. of the first recrystallized material from the preceding paragraph [i.e., the material enriched in the salt of d 2-(6-methoxy-2-naphthyl)propionic acid with N-iso-butyl-D-glucamine] is dissolved in 16 ml. of 5% aqueous isopropanol at about the reflux temperature of the solvent. The solution is cooled to room temperature to give 0.77 g. of a second recrystallized material (m.p. 156°-157° C.). A sample of the latter is treated with hydrochloric acid as set forth in the first paragraph of this Example to give a material even further enriched in d 2-(6-methoxy-2-naphthyl)propionic acid ($[\alpha]_D + 47.9°$).

0.67 G. of the second recrystallized material from the preceding paragraph [i.e., the material further enriched in the salt of d 2-(6-methoxy-naphthyl)propionic acid with N-iso-butyl-D-glucamine] is dissolved in 16 ml. of 5% aqueous isopropanol and 1.0 ml. of water at about the reflux temperature of the solvent. The solution is cooled to room temperature to give 0.39 g. of a third recrystallized material (m.p. 157°-158° C.). The latter is treated with hydrochloric acid as set forth in the first paragraph of this Example to give a material yet further enriched in d 2-(6-methoxy-2-naphthyl)propionic acid ($[\alpha]_D + 54.3°$).

EXAMPLE 11

2.60 G of d,l 2-(6-methoxy-2-naphthyl)propionic acid is heated with 0.50 g. of triethylamine (0.5 equivalent) in 15 ml. of isopropanol and 0.5 ml of water to about the reflux temperature of the solvent to dissolve the d,l 2-(6-methoxy-2-naphthyl)propionic acid. There is an immediate precipitate when 1.32 g. of N-cyclohexyl-D-glucamine (0.5 equivalent) is added to the heated solution. An additional 15 ml. of isopropanol and 1.5 ml. of water are added and the mixture is heated to about the reflux temperature of the solvent to dissolve the precipitate. The solution is cooled to room temperature to give 2.24 g. of a material enriched in the salt of d 2-(6-methoxy-2-naphthyl)propionic acid with N-cyclohexyl-D-glucamine (m.p. 157°-158° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 38.7°$).

1.00 G. of the material enriched in the salt of d 2-(6-methoxy-2-naphthyl)propionic acid with N-cyclohexyl-D-glucamine is dissolved in 20 ml. of 5% aqueous isopropanol at about the reflux temperature of the solvent. The solution is cooled to room temperature to give 0.79 g. of a first recrystallized material (m.p. 159°-160° C.). A sample of the latter is treated with hydrochloric acid as set forth in the preceding paragraph to give a material further enriched in d 2-(6-methoxy-2-naphthyl)propionic acid ($[\alpha]_D + 51.7°$).

0.20 G. of the first recrystallized material from the preceding paragraph [i.e. the material enriched in the salt of d 2-(6-methoxy-2-naphthyl)propionic acid with N-cyclohexyl-D-glucamine] is dissolved in 4 ml. of 5% aqueous isopropanol at about the reflux temperature of the solvent. The solution is cooled to room temperature to give 0.18 g. of a second recrystallized material (m.p. 160°-161° C.). A sample of the latter is treated with hydrochloric acid as set forth in the first paragraph of this Example to give a material even further enriched in d 2-(6-methoxy-2-naphthyl)propionic acid ($[\alpha]_D + 60.3°$).

0.15 G. of the second recrystallized material from the preceding paragraph [i.e. the material further enriched in the salt of d 2-(6-methoxy-2-naphthyl)-propionic acid with N-cyclohexyl-D-glucamine] is dissolved in 5 ml. of 5% aqueous isopropanol at about the reflux temperature of the solvent. The solution is cooled to room temperature to give 0.13 g. of a third recrystallized material (m.p. 161°-162° C.). The latter is treated with hydrochloric acid as set forth in the first paragraph of this Example to give substantially pure d 2-(6-methoxy-2-naphthyl)propionic acid ($[\alpha]_D 65.5°$).

EXAMPLE 12

4.60 G. of d,l 2-(6-methoxy-2-naphthyl)propionic acid is heated with 1.01 g. of triethylamine (0.5 equivalent) in 30 ml. of isopropanol and 1.5 ml. of water to about the reflux temperature of the solvent to dissolve the d,l 2-(6-methoxy-2-naphthyl)propionic acid. 2.93 G. of N-n-octyl-D-glucamine (0.5 equivalent) are added and the solution is cooled to room temperature to give 4.42 g. of a material enriched in the salt of d 2-(6-methoxy-2-naphthyl)propionic acid with N-n-octyl-D-glucamine (m.p. 139°-140° C.). A sample of the latter is dissolved in about 25 ml. of water heated to about 80° C., treated with hydrochloric acid until acidic at which time a material enriched in d 2-(6-methoxy-2-naphthyl)-propionic acid precipitates out of solution and is recovered by filtration ($[\alpha]_D + 54.8°$).

1.00 G. of the material enriched in the salt of d 2-(6-methoxy-2-naphthyl)propionic acid with N-n-octyl-D-glucamine is dissolved in 9.5 ml. of isopropanol and 0.5 ml. of water at about the reflux temperature of the solvent. The solution is cooled to room temperature to give 0.85 g. of a recrystallized salt (m.p. 140°–141° C.). This material is treated with hydrochloric acid as set forth in the preceding paragraph to give substantially pure d 2-(6-methoxy-2-naphthyl)propionic acid ($[\alpha]_D + 65.8°$).

EXAMPLE 13

0.10 G. of the material enriched in the salt of d 2-(6-methoxy-2-naphthyl)propionic acid with N-n-octyl-D-glucamine from the first paragraph of Example 12 and 0.3 g. of potassium hydroxide in 25 ml. of water are stirred for one hour at room temperature. The precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 55.3°$).

EXAMPLE 14

2.30 G. of d,l 2-(6-methoxy-2-naphthyl)propionic acid is heated with 0.50 g. of triethylamine (0.5 equivalent) in 30 ml. of ethylene glycol to 90° C. to dissolve the d,l 2-(6-methoxy-2-naphthyl)propionic acid. 1.47 g. of N-n-octyl-D-glucamine are added and the solution is cooled to 40° C. and seeded with crystals of the salt of d 2-(6-methoxy-2-naphthyl)propionic acid with N-n-octyl-D-glucamine. The reaction mixture is stirred overnight at room temperature to give 1.47 g. of a material enriched in the salt of d 2-(6-methoxy-2-naphthyl)propionic acid with N-n-octyl-D-glucamine (m.p. 115°–122° C.). A sample of the latter is dissolved in about 25 ml. of water heated to about 80° C., treated with hydrochloric acid until acidic at which time a material enriched in d 2-(6-methoxy-2-naphthyl)propionic acid precipitates out of solution and is recovered by filtration ($[\alpha]_D + 65.5°$).

EXAMPLE 15

2.30 G. of d,l 2-(6-methoxy-2-naphthyl)propionic acid is heated with 0.50 g. of triethylamine (0.5 equivalent) in 15 ml. of isopropanol and 0.75 ml. of water to about the reflux temperature of the solvent to dissolve the d,l 2-(6-methoxy-2-naphthyl)propionic acid. 1.75 G. of N-n-dodecyl-D-glucamine (0.5 equivalent) are added and the solution is cooled to room temperature to give 2.50 g. of a material enriched in the salt of d 2-(6-methoxy-2-naphthyl)propionic acid with N-n-dodecyl-D-glucamine (m.p. 133°–135° C.). A sample of the latter is suspended in about 25 ml. of water at room temperature in the presence of 300 mg. of potassium hydroxide and held at that temperature for 60 minutes. The precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 56.1°$).

1.00 G. of the material enriched in the salt of d 2-(6-methoxy-2-naphthyl)propionic acid with N-n-dodecyl-D-glucamine is dissolved in 20 ml. of 5% aqueous isopropanol at about the reflux temperature of the solvent. The solution is cooled to room temperature to give 0.88 g. of a first recrystallized material (m.p. 135°–137° C.). A sample of the latter is treated with potassium hydroxide then hydrochloric acid as set forth in the preceding paragraph to give a material also enriched in d 2-(6-methoxy-2-naphthyl)propionic acid ($[\alpha]_D + 58.9°$).

0.62 G. of the first recrystallized material from the preceding paragraph [i.e. the material also enriched in the salt of d 2-(6-methoxy-2-naphthyl)propionic acid with N-n-dodecyl-D-glucamine] is dissolved in 15 ml. of 5% aqueous isopropanol at about the reflux temperature of the solvent. The solution is cooled to room temperature to give 0.59 g. of a second recrystallized material (m.p. 135°–137° C.).

0.51 G. of the second recrystallized material from the preceding paragraph [i.e., the material further enriched in the salt of d 2-(6-methoxy-2-naphthyl)propionic acid with N-n-dodecyl-D-glucamine] is dissolved in 10 ml. of 5% aqueous isopropanol at about the reflux temperature of the solvent. The solution is cooled to room temperature to give 0.43 g. of a third recrystallized material (m.p. 135°–137° C.). The latter is treated with potassium hydroxide then hydrochloric acid as set forth in the first paragraph of this Example to give a material yet further enriched in d 2-(6-methoxy-2-naphthyl)propionic acid ($[\alpha]_D + 67.6°$).

EXAMPLE 16

1.15 G. of d,l 2-(6-methoxy-2-naphthyl)propionic acid is heated with 0.25 g. of triethylamine (0.5 equivalent) in 10 ml. of isopropanol to about the reflux temperature of the solvent to dissolve the d,l 2-(6-methoxy-2-naphthyl)propionic acid. 1.09 G. of N-n-octadecyl-D-glucamine (0.5 equivalent) are added, and the solution filtered while hot to remove some turbidity, cooled slightly, then seeded with a small amount of the salt of d 2-(6-methoxy-2-naphthyl)propionic acid with N-n-octadecyl-D-glucamine, and then cooled to room temperature to give 1.55 g. of a material enriched in the salt of d 2-(6-methoxy-2-naphthyl)propionic acid with N-n-octadecyl-D-glucamine (m.p. 123°–127° C.). A sample of the latter is suspended in about 25 ml. of water at room temperature in the presence of 300 mg. of potassium hydroxide and held at that temperature for 60 minutes. The precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 57.9°$).

1.0 G. of the material enriched in the salt of d 2-(6-methoxy-2-naphthyl)propionic acid with N-n-octadecyl-D-glucamine is stirred in 10 ml. of isopropanol at about the reflux temperature of the solvent. The solution is cooled to room temperature over two hours to give 0.95 g. of a first recrystallized material (m.p. 129°–130° C.). A sample of the latter is treated with potassium hydroxide then hydrochloric acid as set forth in the preceding paragraph to give a material further enriched in d 2-(6-methoxy-2-naphthyl)propionic acid ($[\alpha]_D + 68.1°$).

EXAMPLE 17

100 Mg. of the sodium salt of d,l-2-(6-methoxy-2-naphthyl)propionic acid is heated with 100 mg. of the hydrochloride salt of N-n-butyl-D-glucamine in 2 ml. of 5% aqueous isopropanol to about the reflux temperature of the solvent. The reaction mixture is slowly cooled, seeded with a small amount of the salt of d 2-(6-methoxy-2-naphthyl)propionic acid with N-n-butyl-D-glucamine, and then curther cooled to room temperature to give, after recovery by filtration and washing, 1.10 g. of a material enriched in the salt of d 2-(6-methoxy-2-naphthyl)-propionic acid with N-n-butyl-D-glucamine (m.p. 143°–145° C.). A sample of the latter is dissolved in water, and treated with hydrochloric acid until acidic at which time a material enriched in d 2-(6-methoxy-2-naphthyl)propionic acid precipitates out of solution and is recovered by filtration ($[\alpha]_D + 54.9°$).

EXAMPLE 18

The solubilities of the diastereoisomeric salt pairs of d 2-(6-methoxy-2-naphthyl)propionic acid and l 2-(6-methoxy-2-naphthyl)propionic acid with various N-R-D-glucamines in methanol at room temperature and at reflux are given in the following Table:

TABLE 1

| | SOLUBILITY IN MeOH (g/100 ml. of solvent) | | | |
|---|---|---|---|---|
| | d 2-(6-methoxy-2-naphthyl)propionic acid with N-R-D-glucamine | | l 2-(6-methoxy-2-naphthyl)propionic acid with N-R-D-glucamine | |
| R | 23° C. | reflux | 23° C. | reflux |
| ethyl | 0.83 | | 5.1 | |
| n-propyl | 0.31 | 1.7 | 6.8 | |
| iso-propyl | 2.3 | 6.4 | 6.7 | 95 |
| n-butyl | 1.3 | 9.2 | 5.0 | 90 |
| iso-butyl | 1.2 | | 10.8 | |
| cyclohexyl | 2.1 | | 23.1 | |
| n-octyl | 1.8 | 21.1 | 21.7 | |
| n-dodecyl | 0.32 | | 8.7 | |

EXAMPLE 19

2.30 G. of d,l 2-(6-methoxy-2-naphthyl)propionic acid is heated with 0.45 g. of triethylamine (0.45 equivalent) in 40 ml. of isopropanol and 1.0 ml. of water to about 80° C. to dissolve the d,l 2-(6-methoxy-2-naphthyl)propionic acid. 1.46 G. of N-n-hexyl-D-glucamine (0.55 equivalent) is added and the solution is cooled to room temperature to give 2.48 g. of a material enriched in the salt of d 2-(6-methoxy-2-naphthyl)-propionic acid with N-n-hexyl-D-glucamine (m.p. 131°–132° C.). A sample of the latter is suspended in about 25 ml. of water at room temperature, acidified with hydrochloric acid and stirred at that temperature for about 60 minutes. The resultant precipitate, a material enriched in d 2-(6-methoxy-2-naphthyl)propionic acid, is recovered by filtration ($[\alpha]_D + 37.2°$).

1.00 G. of the material enriched in the salt of d 2-(6-methoxy-2-naphthyl)propionic acid with N-n-hexyl-D-glucamine is dissolved in 10 ml. of 5% aqueous isopropanol at about the reflux temperature of the solvent. The solution is cooled to room temperature to give 0.75 g. of a first recrystallized salt (m.p. 130°–131° C.). This material is treated with hydrochloric acid as set forth in the preceding paragraph to give substantially pure d 2-(6-methoxy-2-naphthyl)-propionic acid ($[\alpha]_D + 66.2°$).

EXAMPLE 20

1.00 G. of the material in the salt of d 2-(6-methoxy-2-naphthyl)propionic acid with N-n-hexyl-D-glucamine from the first paragraph of Example 19 is suspended in 10 ml. of water. 0.15 G. of potassium hydroxide are added and the mixture stirred at room temperature for 1.5 hours. The resultant precipitate is collected, washed with 5 ml. of water, and dried to give 0.38 g. of N-n-hexyl-D-glucamine (m.p. 124°–126° C.). D 2-(6-methoxy-2-naphthyl)propionic acid is recoverd from the filtrate by treatment with hydrochloric acid as set forth in the first paragraph of Example 19.

EXAMPLE 21

1.00 G. of the material enriched in the salt of d 2-(6-methoxy-2-naphthyl)propionic acid with N-n-hexyl-D-glucamine from the first paragraph of Example 19 is suspended in 8 ml. of water. 0.15 G. of potassium hydroxide are added and the mixture stirred at room temperature for 45 minutes. The resultant precipitate is collected, washed with 2 ml. of water, and dried under vacuum (with a slight nitrogen bleed) at 45° C. to give 0.47 g. of N-n-hexyl-D-glucamine (m.p. 122°–124° C.). D 2-(6-methoxy-2-naphthyl)propionic acid is recovered from the filtrate by treatment with hydrochloric acid as set in the first paragraph of Example 19.

EXAMPLE 22

2.30 G. of d,l 2-(6-methoxy-2-naphthyl)propionic acid is heated with 1.46 g. of N-n-hexyl-D-glucamine (0.55 equivalent) in 15 ml. of water to about 80° C. 0.17 G. of potassium hydroxide (0.45 equivalent) are added and the pH of the solution adjusted to 8 with potassium carbonate. The solution is seeded with a small amount of the salt of d 2-(6-methoxy-2-naphthyl)propionic acid with N-n-hexyl-D-glucamine and cooled to give 1.25 g. of a material enriched in the salt of d 2-(6-methoxy-2-naphthyl)propionic acid with N-n-hexyl-D-glucamine (m.p. 125°–127° C.

EXAMPLE 23

4.60 G. of d,l 2-(6-methoxy-2-naphthyl)propionic acid is heated with 0.91 g. of triethylamine (0.45 equivalent) in 60 ml. of isopropanol to about the reflux temperature of the solvent to dissolve the d,l 2-(6-methoxy-2-naphthyl)propionic acid. 3.22 G. of N-n-octyl-D-glucamine (0.55 equivalent) are added, the solution is cooled slightly and then seeded with a small amount of the salt d 2-(6-methoxy-2-naphthyl)propionic acid with N-n-octyl-D-glucamine to give a precipitate. The reaction mixture is aged at 60° C. for 1.5 hours, then cooled overnight to room temperature to give, after washing with 20 ml. of isopropanol, 4.9 g. of a material enriched in the salt of d 2-(6-methoxy-2-naphthyl)propionic acid with N-n-octyl-D-glucamine (m.p. 138°–139° C.). A sample of the latter is suspended in about 25 ml. of water at room temperature in the presence of 300 mg. of potassium hydroxide and held at that temperature for about 60 minutes. The resultant precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 64.3°$).

EXAMPLE 24

4.60 G. of d,l 2-(6-methoxy-2-naphthyl)propionic acid is slurried with 25 ml. of water and 0.60 g. of potassium hydroxide (0.45 equivalent) at 70° C. for 10 minutes. 3.22 G. of N-n-octyl-D-glucamine (0.55 equivalent) are added and the solution is cooled slowly to 50° C. A small amount of the salt of d 2-(6-methoxy-2-naphthyl)propionic acid with N-n-octyl-D-glucamine is added and the solution cooled overnight, with stirring, to room temperature to give, after recovery by filtration, 4.0 g. of a material enriched in the salt of d 2-(6-methoxy-2-naphthyl)propionic acid with N-n-octyl-D-glucamine (m.p. 138°–140° C.). A sample of the latter is suspended in about 25 ml. of water at room temperature in the presence of 300 mg. of potassium hydroxide and held at that temperature for about 60 minutes. The resultant precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 62.9°$).

EXAMPLE 25

The procedure of Example 24 is repeated using 20 ml. of water to yield 4.05 g. of a material enriched in the salt of d 2-(6-methoxy-2-naphthyl)propionic acid with N-n-octyl-D-glucamine (m.p. 138°–140° C.). The latter is treated with potassium hydroxide then hydrochloric acid as set forth in Example 24 to give a material enriched in d 2-(6-methoxy-2-naphthyl)propionic acid ($[\alpha]_D + 65.1°$).

EXAMPLE 26

The procedure of Example 24 is repeated using 15 ml. of water to yield 4.45 g. of a material enriched in the salt of d 2-(6-methoxy-2-naphthyl)propionic acid with N-n-octyl-D-glucamine (m.p. 138°–140° C.). The latter is treated with potassium hydroxide then hydrochloric acid as set forth in Example 24 to give a material enriched in d 2-(6-methoxy-2-naphthyl)propionic acid ($[\alpha]_D + 63.5°$).

EXAMPLE 27

44.5 G. of a material enriched in the salt of d 2-(6-methoxy-2-naphthyl)propionic acid with N-n-octyl-D-glucamine is treated with 6.2 g. of potassium hydroxide in 455 ml. of water. The reaction mixture is stirred at 46° C. for 2 hours, then cooled slowly to 36° C., with stirring, over one additional hour. The reaction mixture is held at room temperature for about 60 hours.

The resultant precipitate is collected by filtration and washed with 150 ml. of water to give 24.6 g. (99% of theory) of N-n-octyl-D-glucamine (m.p. 212°–123° C.).

The filtrate is treated with 12 ml. of concentrated hydrochloric acid to give a fine, thick precipitate. This precipitate is aged, with stirring, with an additional 350 ml. of water, then filtered, washed with water and dried at 45° C. to give 19.4 g. (99% of theory) of d 2-(6-methoxy-2-naphthyl)propionic acid (m.p. 147°–150° C.

EXAMPLE 28

2.30 G. of d,1 2-(6-methoxy-2-naphthyl)propionic acid is heated in 27.3 ml. of isopropanol and 2.7 ml. of water to about the reflux temperature of the solvent to dissolve the d,1 2-(6-methoxy-2-naphthyl)propionic acid. 2.93 G. of N-n-octyl-D-glucamine (1.0 equivalent) are added and the solution is cooled to room temperature to give, after washing with 2 ml. of aqueous isopropanol, 2.57 g. of a material enriched in the salt of d 2-(6-methoxy-2-naphthyl)propionic acid with N-n-octyl-D-glucamine (m.p. 138°–140° C.). A sample of the latter is suspended in about 25 ml. of water at room temperature in the presence of 300 mg. of potassium hydroxide and held at that temperature for about 60 minutes. The resultant precipitate is removed by filtration. The filtrate is treated with hydrochloric acid until acidic at which time a material enriched in d 2-(6-methoxy-2-naphthyl)propionic acid precipitates out of solution and is recovered by filtration ($[\alpha]_D + 61.7°$).

EXAMPLE 29

2.0 Kg of d,1 2-(6-methoxy-2-naphthyl)propionic acid is added to a mixture of 9.08 l. of methanol and 0.92 l. of toluene. This mixture is heated to 55° C. and 2.54 kg of N-n-octyl-D-glucamine is added. The slurry is heated to reflux, at which temperature all solids are in solution. The mixture is cooled to 56° C. and 2.5 g. of the salt of d 2-(6-methoxy-2-naphthyl)propionic acid with N-n-octyl-D-glucamine is added. After aging at 55°–56° C. for one hour, the slurry is cooled to 25° C. at a rate of 10° C./hour. 3.0 Kg. of a wet cake of the salt of d 2-(6-methoxy-2-naphthyl)propionic acid with N-n-octyl-D-glucamine is recovered by filtration and washed with 6.0 l. of methanol.

The wet cake from the preceding step is charged to a mixture of 11.0 l. of water and 0.25 l. of hexane and heated to 50° C. 300 G. of potassium hydroxide is added and the mixture is held for one hour at 50° C. The slurry is cooled to 25° C. at a rate of 10° C./hour. The precipitated N-n-octyl-D-glucamine is filtered, washed with 3 l. of water and dried (yield: 1.11 kg.).

The combined filtrate and washes from the preceding step are added to 100 ml. of toluene and 420 ml. of concentrated hydrochloric acid (to a pH of less than 1.0). The slurry is heated to 70° C., aged for one hour and cooled to 25° C. at a rate of 10° C./hour. The precipitated 2-(6-methoxy-2-naphthyl)propionic acid is recovered by filtration and washed with 2.0 l. of water. This material is of sufficient purity that further recrystallizations to increase the optical purity thereof are not necessary.

The d 2-(6-methoxy-2-naphthyl)propionic acid is dissolved in 4.40 l. of acetone and 22.5 g. of carbon are added. The solution is stirred for one hour, then filtered. The filter is washed with 2.0 l. of acetone. The combined filtrate and washes are concentrated under vacuum to a volume of about 1.0 l. and a solution of 60 ml. of concentrated hydrochloric acid in 400 ml. of water is added, followed by a futher addition of 5.3 l. of water. The slurry is aged for one hour at 20° C. and the precipitated d 2-(6-methoxy-2-naphthyl)propionic acid recovered by filtration, washed with 5.0 l. of water and dried (yield 838.0 grams; 41.9% w/w based on d,1 2-(6-methoxy-2-naphthyl)propionic acid charged; m.p. 153.5°–156.0° C.; $[\alpha]_D + 66.6°$). This recrystallization is solely for the purposes of removing extraneous insoluble material, if any, and improving the color of the precipitated product.

The filtrates and washes from the preceding step are combined and distilled to a volume of 5.5 l. Distillation is continued, with water being added to maintain the volume at 5.5 l. When all the methanol had distilled off, 1 l. of water is added, followed by the addition of 334 g. of potassium hydroxide. The mixture is cooled to 60° C., seeded with a small amount of N-n-octyl-D-glucamine and cooled to 25° C. The precipitate N-n-octyl-D-glucamine is recovered by filtration, washed with one l. of water, followed by a second wash with 4 l. of water, and then dried (yield: 1.31 kg.). Overall N-n-octyl-D-glucamine recovery (ie, in this step and from the step in the second paragraph of this Example) is 2.42 kg. (95.2%).

431 G. of potassium hydroxide is charged to the combined filtrates and first wash from the preceding step and the mixture is heated to 130° C. The solution is cooled to 50° C. under 30 psi over three hours and 130 ml. of toluene are added, followed by the addition of 1.4 l. of concentrated hydrochloric acid. The slurry is heated to 80° C., aged for one hour at that temperature, and cooled to 25° C. at a rate of 10° C./hour. The precipitated d,l 2-(6-methoxy-2-naphthyl)propionic acid is recovered by filtration, washed with 10 l. of water and dried [yield: 1122 g. (56.1%)].

What is claimed is:

1. A process for separating d 2-(6-methoxy-2-naphthyl)propionic acid from a mixture of d and l 2-(6-methoxy-2-naphthyl)propionic acid or salts thereof comprising:

preparing a mixture of d and l 2-(6-methoxy-2-naphthyl)propionic acid or soluble salts thereof and N-R-D-glucamine or a salt thereof, where R is alkyl having 2 to 36 carbon atoms or cycloalkyl having 3 to 8 carbon atoms, in an inert solvent to form the salts of d and l 2-(6-methoxy-2-naphthyl)-propionic acid with N-R-D-glucamine, the salt of d 2-(6-methoxy-2-naphthyl)-propionic acid with the N-R-D-glucamine being significantly less soluble in the inert solvent than is the salt of l 2-(6-methoxy-2-napthyl)propionic acid with the N-R-D-glucamine at the temperature of crystallization, and crystallizing the salt of d 2-(methoxy-2-naphthyl)-propionic acid with N-R-D-glucamine from said mixture to yield a salt product enriched in the salt of d 2-(6-methoxy-2-naphthyl)propionic acid with N-R-D-glucamine.

2. The process of claim 1 wherein said mixture is heated to solubilize the salts of d and l 2-(6-methoxy-2-naphthyl)propionic acid with N-R-D-glucamine in said inert solvent, and said salt of d 2-(6-methoxy-2-naphthyl)propionic acid with N-R-D-glucamine is crystallized by cooling said heated mixture so as to subject said mixture to fractional crystallization to thereby obtain said salt product enriched in the salt of d 2-(6-methoxy-2-naphthyl)propionic acid with N-R-D-glucamine.

3. The process of claim 1 further including the steps of dissolving said crystalline salt product enriched in the salt of d 2-(6-methoxy-2-naphthyl)-propionic acid with N-R-D-glucamine in an inert solvent therefor, cleaving said salt to yield d 2-(6-methoxy-2-naphthyl)-propionic acid, and crystallizing substantially pure d 2-(6-methoxy-2-naphthyl)propionic acid therefrom.

4. The process of claim 2 further including the steps of dissolving said crystalline salt product enriched in the salt of d 2-(6-methoxy-2-naphthyl)-propionic acid with N-R-D-glucamine in an inert solvent therefor, cleaving said salt to yield d 2-(6-methoxy-2-naphthyl)-propionic acid, and crystallizing substantially pure d 2-(6-methoxy-2-naphthyl)propionic acid therefrom.

5. The process of claims 1, 2, 3 or 4 wherein R is alkyl having 2 to 18 carbon atoms.

6. The process of claims 1, 2, 3 or 4 wherein R is n-propyl, n-butyl or n-octyl.

7. The process of claims 1, 2, 3 or 4 wherein R is cycloalkyl having 3 to 8 carbon atoms.

8. The process of claims 1, 2, 3 or 4 wherein R is cyclohexyl.

9. The process of claim 1 wherein said mixture includes about 50 to about 100 molar percent of said N-R-D-glucamine based upon the d and l 2-(6-methoxy-2-naphthyl)propionic acid in said mixture.

10. The process of claim 1 wherein said mixture includes about 50-60 molar percent of said N-R-D-glucamine and about 50-40 molar percent of an inorganic base or an organic base, said molar percentages being based upon the d and l 2-(6-methoxy-2-naphthyl)propionic acid in said mixture.

11. The process of claim 10 wherein said inorganic base is sodium hydroxide or potassium hydroxide.

12. The process of claim 10 wherein said organic base is a trialkylamine wherein the alkyl group contains from 1 to 3 carbon atoms.

13. The process of claim 10 wherein said organic base is triethylamine.

14. The process of claims 1 or 2 wherein the solvent comprises an alcohol.

15. The process of claims 1 or 2 wherein the solvent comprises methanol or isopropanol.

16. The process of claims 1 or 2 further including the step of treating the mother liquors remaining after removal of said crystalline salt product therefrom to recover N-R-D-glucamine.

17. The process of claims 1 or 2 further including the steps of recovering a non-racemic mixture of d and l 2-(6-methoxy-2-naphthyl)propionic acid which remains after removal of said crystalline salt product from said mixture, racemizing said non-racemic mixture, and recycling said racemized mixture.

18. The process of claim 1 further including the steps of subjecting said crystalline salt product enriched in the salt of d 2-(6-methoxy-2-naphthyl)-propionic acid with N-R-D-glucamine to at least one additional recrystallization to obtain a product further enriched in the salt of d 2-(6-methoxy-2-naphthyl)-propionic acid with N-R-D-glucamine, and then dissolving said product further enriched in the salt of d 2-(6-methoxy-2-naphthyl)propionic acid with N-R-D-glucamine in an inert solvent therefor, cleaving said product to yield d 2-(6-methoxy-2-naphthyl)propionic acid, and crystallizing substantially pure d 2-(6-methoxy-2-naphthyl)-propionic acid therefrom.

19. The process of claims 3, 4 or 18 further including the step of subjecting said substantially pure d 2-(6-methoxy-2-naphthyl)propionic acid to at least one additonal recrystallization to further increase the purity thereof.

20. The process of claims 1, 2, 3, 4, 9, 10, or 11 wherein said N-R-D-glucamine is N-n-octyl-D-glucamine.

21. The process of claims 1, 2, 3, 4, 9, 10 or 11 wherein R is alkyl having 6 to 18 carbon atoms.

* * * * *